United States Patent [19]

Leibovich et al.

[11] Patent Number: 4,808,402
[45] Date of Patent: Feb. 28, 1989

[54] METHOD AND COMPOSITIONS FOR MODULATING NEOVASCULARIZATION

[75] Inventors: Samuel J. Leibovich, Skokie; Peter J. Polverini, Evanston, both of Ill.; H. Michael Shepard, San Francisco, Calif.

[73] Assignees: Northwestern University, Evanston, Ill.; Genentech, Inc., San Francisco, Calif.

[21] Appl. No.: 56,554

[22] Filed: May 29, 1987

[51] Int. Cl.$^4$ .............................................. A61K 31/74
[52] U.S. Cl. ...................................... 424/423; 424/78; 424/81
[58] Field of Search ........................... 424/78, 81, 423

[56] References Cited

U.S. PATENT DOCUMENTS

| 4,457,916 | 7/1984 | Hayashi et al. | 530/351 |
| 4,465,669 | 8/1984 | Wissler et al. | 435/68 |
| 4,666,705 | 5/1987 | DeCrosta | 424/81 |
| 4,721,672 | 1/1988 | Vallee et al. | 514/12 |

OTHER PUBLICATIONS

Chem. Abstract vol. 106, entry 100647.
Chem. Abstract vol. 105, entry 207395.
Chem. Abstract vol. 105 entry 224304b.
Chem. Abstract vol. 104 entry 4515.
Scientific American vol. 258 May 1988 pp. 67-75.

Primary Examiner—Joseph L. Schofer
Assistant Examiner—Peter F. Kulkosky

[57] ABSTRACT

Tumor necrosis factors possess the unexpected ability to induce angiogenesis, or neovascularization. Novel methods and TNF-containing compositions and articles are provided for the induction of neovascularization and rapid wound healing.

15 Claims, No Drawings

METHOD AND COMPOSITIONS FOR MODULATING NEOVASCULARIZATION

This invention relates to the modulation of neovascularization. In particular, methods and compositions are provided for the enhancement of wound healing by promoting neovascularization.

Neovascularization, also known as angiogenesis, is a complex process involving several sequential steps including basement membrane degradation, endothelial cell mobilization and proliferation, vessel canalization, and new basement membrane formation (Mantovani, A. "Int. J. Cancer" 25:617 [1980]). A variety of mediators, both tumor- and nontumor-derived, appear capable of initiating portions of this reaction sequence (Auerbach, R., "Angiogenesis-Inducing Factors: A Review" in Lymphokines, Vol. 4, edited by Pick, E., p. 69, New York Academic Press, [1981] and Bullino, P. "J. Natl. Cancer Inst." 61:639 [1978]). Such substances include Fibroblast Growth Factor (Shing, Y. et al., "J. Cell. Biochem." 29:275-287 [1985]; Thomas, K. A. et al., "Proc. Natl. Acad. Sci. USA" 82:6409-6413 [1985] and Esch, F. et al., "Proc. Natl. Acad. Sci. USA" 82:6507-6511 [1985]), angiogenin (Fett, J. W. et al., "Biochemistry" 24:5480-5486 [1985]), Epidermal Growth Factor (Schreiber, A. B. et al., "Science" 232:1250-1252 [1986]) and Transforming Growth Factor-α (Schreiber, A. B. et al., supra). Another growth factor, Transforming Growth Factor -β, is potently chemotactic for macrophages and induces their expression of angiogenic activity (Wiseman, D. et al., submitted for publication). Macrophages are known to be a component of a number of pathologic and physiologic processes in which fibrovascular proliferation is an important component. These cells are thought to play a key role in mediating the proliferative events involved in these responses.

Macrophages have been shown to play important roles in mediating tumor neovascularization, a vital stage in the growth of solid tumors (Polverini, P. J. et al. "Lab. Invest." 51:635-642 [1985]), as well as in wound repair (Leibovich, S. J. et al. "Am. J. Pathol. 78:71-100 [1975]; Clark, R. A. et al. "Surg. Forum" 27:16-22 [1976] and Banda, M. J. et al., "Proc. Natl. Acad. Sci. USA" 79:7773-7777 [1982]) and chronic inflammatory conditions such as rheumatoid arthritis (Koch, A. E. et al. "Arthr. Rheum." 29:471-479 [1986]).

Macrophages, or monocytes have been associated with angiogenic activity, but the molecule(s) responsible for this activity remain largely uncharacterized. Macrophage angiogenic activity can be induced by activation of macrophages (Koch, A. E. et al., "J. Leukocyte Biol." 39:233-238[1986]). More specifically, macrophages produce a mesenchymal growth factor, called macrophage-derived growth factor (S. Liebovich et al., "Am. J. Pathol." 84:501 [1976] and A. Mantovani "Int. J. Cancer" 22:741 [1978]). Macrophage-derived growth factor has been partially purified from cultures of rat peritoneal macrophages and from cultures of several macrophage-like cell lines. Such partially purified preparations possess mitogenic activity for endothelial cells in vitro, as well as angiogenic activity in vivo in the corneal neovascularization assay (S. Leibovich, *Tissue Repair: Biological and Clinical Aspects of Soft and Hard Tissue Repair* T. Hunt, Ed., p. 351 [1984]). Recently, Banda et al. (Proc. Natl. Acad. Sci. USA 79:7773 [1982]) have reported that exudate fluid isolated from rabbit skin wounds contains a relatively low molecular weight (2,000 to 14,000 daltons) angiogenic activity which may be of macrophage derivation. This material stimulated directional migration of rabbit brain capillary endothelial cells in Boyden chamber assays in vitro but was nonmitogenic.

Monocytes and lymphocytes are known to produce a number of effector molecules, including the cytokines tumor necrosis factor (TNF)-α (Aggarwal, B. B. et al. "J. Biol. Chem." 260:2345 [1985]) and tumor necrosis factor (TNF)-β(previously called lymphotoxin) (Aggarwal. B. B. et al., "J. Biol. Chem." 259:686 [1984] and Aggarwal, B. B. et al., "J. Biol. Chem." 260:2334 [1985]) respectively. The complete primary amino acid sequences for these cytokines have been determined and the cDNAs of both TNF-β (Gray, P. W. et al., "Nature" 312:721 [1984]) and TNF-α (Pennica, D. et al., "Nature" 312:724 [1984]; Shirai, T. et al., "Nature" 313:803 [1985]; Wang, A. M. et al., "Science" 228:149 [1985] and Marmenoit, A. et al., "Eur. J. Biochem." 152:515 [1985]) have been cloned by recombinant DNA methods and expressed in *E. coli.*

In vivo and in vitro studies using the pure TNFs have shown that both TNF-α and TNF-β possess the unique ability to kill some tumor cells selectively, while sparing most normal cells. In addition to their antitumor activity, these proteins mediate a diverse array of biological responses in vitro. Although their true in vivo significance is still unknown, the biologic studies strongly suggest that TNF-α and TNF-β play an important role in immunomodulatory and inflammatory responses.

TNF-α and TNF-β differ significantly in their physical and chemical properties. TNF-α is a 157 residue polypeptide with a molecular weight of about 17,000 (Aggarwal, B. B. et al., "J. Biol. Chem." 260:2345 [1985]) by SDS-PAGE. Under the same conditions, two different forms of TNF-β, with molecular weights of about 20,000 (148 residues) and 25,000 (171 residues), have been found (Aggarwal et al. supra). The 20 kD species is a proteolytic cleavage product of the 25 kD form (Aggarwal et al. supra). The molecular weight of TNFs under non-denaturing conditions are very different. Purified human TNF-α has a native molecular weight of 45,000, whereas TNF-β elutes at a position corresponding to a molecular weight of 60–70,000 during gel filtration. The isoelectric points (pI) of these cytotoxic factors have been reported to be in the range of 4.5–6.5. TNF-β has a pI of 5.8, and 5.3 is the pI determined for TNF-α.

The amino acid sequence of human TNF-α as determined from the protein (Shirai, T. et al., supra; Wang, A. M. et al., supra; and Yamada, Y. et al., "J. of Biotechnology" 3:141 [1985]) or predicted from the nucleotide sequence (Shirai, T. et al., supra; Wang, A. M. et al., supra; Yamada, Y. et al., supra; and Marmenoit, A. et al. supra) has been described. Some variations in the protein sequences at the amino terminal end have been observed. The N-terminal protein sequence of the natural human TNF-α purified from HL-60 cells obtained by Wang et al., (supra) departs by two residues from the sequence reported earlier (Aggarwal, B. B. et al. supra) and that predicted from the cloned cDNA sequence (Pennica, D. et al. supra and Wang. A. M. et al. supra). Two out of the three serines in positions 3–5 of the mature protein are missing, and the His-Val sequence in position 15 and 16 has been replaced by Val-Ser-Val-Ser. The reason for this discrepancy is not clear. Two groups (Shirai, T. et al. supra and Yamada Y. et al.

supra) have reported the N-terminal sequence of recombinant human TNF-α expressed and purified in *E. coli* in which Val-Arg from position 1 and 2 of the natural protein sequence, respectively, are missing, even though the nucleotide codons for these amino acids are present at the corresponding positions in both the genomic (Shirai, T. et al., supra) and cDNA (Yamada, Y. et al., supra) sequences. These investigations assumed that the N-terminal sequence of human TNF-α was Ser-Ser-Ser-Arg- . . . based on an analogy with the sequence of rabbit TNF-α purified from serum.

TNF-α has been extensively studied and has been found to exert a variety of effects on normal cells. One major indication of an effect of TNF-α on normal tissue stems from studies on cachectin (Buetler, B. A. et al. "J. Immunol." 135:3972[1985]; Buetler, B. A. et al. "Nature" 316:552 ]1985] and Torti, F. M. et al., "Science" 229:867 [1985]), a macrophage secreted factor that inhibited the synthesis of lipoprotein lipase in the mouse adipocyte cell line 3T3-L1. Cachectin has been suggested to be the agent responsible for causing cachexia during certain chronic host infections and malignancies (Torti, F. M. et al. supra and Buetler, B. et al., "Science" 229:869 [1985]). One of the salient features of cachexia is the loss of body weight, even with adequate food consumption. The purification of cachectin and its partial structure determination revealed that this protein was identical to TNF-α (Buetler, B. A. et al., "J. Immunol." and "Nature" supra) These studies have prompted the suggestion that TNF-α is the agent responsible for cachexia during chronic host infection (Torti, F. M. et al., supra and Buetler, B. A. et al., "Science" supra). However, recent studies indicate that this activity is not unique to TNF-α, since other cytokines including IL-1 (Buetler, B. A. et al.. "J. Immunol." 135:3969 [1985]) and IFNs (Keay, S. et al. "Proc. Natl. Acad. Sci. USA" 77:4099 [1980] also can suppress lipoprotein lipase activity in 3T3-L1 adipocytes.

TNF-like tumor necrosis serum (TNS) and partially purified preparations have been reported to protect animals against bacterial and parasitic infections. C3H/HeJ mice challenged with *Klebsiella pneumoniae* or *Listeria monocytogenes* showed increased survival rates following TNS injection compared to untreated controls (Parent, M. et al., "Recent Results Cancer Res." 75:213 [1980]). TNF-like activity also appears to have a potent cytotoxic effect on the malarial parasites *Plasmodium falciparum* (Hardaris, C. G. et al., "Infect. and Immun." 42:385 [1983]), *Plasmodium yoelii* and *Plasmodium berghei* (Taverne, J. et al., "Clin. Exp. Immunol." 57:293 [1984]). Recently recombinant TNF-α was shown to be similar to eosinophil cytoxicity enhancing factor and it potentiated eosinophil cytotoxicity against *Schistosoma mansoni* larvae (Silberstein, D. et al., "Proc. Natl. Acad. Sci. USA" 83:1055 [1986]).

Several investigators (Kohase, M. et al., "Cell" 45: [1986]; Mestan, J. et al. "Nature" 323:816 [1986]; and Wong, G. C. et al., "Nature" 323:819 [1986]) have found that rTNF-α exhibits direct antiviral activity similar to interferons. TNF-α protected HEP-2 cells against VSV infection and this effect was not blocked by anti-IFN antibodies (Mestan, J. et al. supra). Similarly, TNF-α and TNF-β were shown to directly induce resistance to infection by both RNA viruses (EMCV and VSV) and DNA viruses (Ad-2 and HSV-2) in diverse cell types (Wong, G. C. et al. supra). The antiviral effect of TNFs was not IFN-mediated since it was not abolished by anti-IFN-α, -β or -γ antibodies, there were no detectable levels of IFNs in the cell culture fluids, and no IFN mRNA was found in the cells. In addition to inducing the antiviral state, TNFs were also able to selectively kill virus-infected cells. Both the antiviral activity and the virus-induced cytotoxicity of TNFs were synergistically enhanced by IFNs (Wong, G. C. et al. supra). Furthermore, viruses as well as the polymer poly(I):-poly(C) could induce the production of TNF-α in HL-60 cells and TNF-β in RPMI 1788 cells (Wong, G. C. et al. supra).

A role for TNF in mediating inflammatory responses has been implied from TNF's effects on neutrophil functions. It has been reported (Shalaby, M. R. et al., "J. Immunol." 135:2069 [1985]) that pretreatment of PMN with purified TNF-α and TNF-β (free of detectable LPS contamination) induces a significant increase in their ability to phagocytose fluorescein-conjugated latex beads as well as an enhancement of PMN-mediated antibody dependent cellular cytotoxicity (ADCC) against chicken erythrocytes. More recently other investigators (Klebanoff, S. J. et al., "J. Immunol." 136:4220 [1986]) have found significant increases in phagocytosis of unopsonized zymosan particles, degranulation, and respiratory burst activity by TNF-α treated PMN. Interestingly, these effects were inhibited by monoclonal antibodies against the C3bi receptor/adherence glycoprotein CD11 (Harlan, J. M. et al. "Blood" 66:167 [1985]). TNF-α has been shown (Gamble, J. R. et al. "Proc. Natl. Acad. Sci. USA" 82:8667 [1985]) to increase the expression of this protein on neutrophils resulting in their enhanced adherence to the endothelium.

In addition to its effects on PMN, TNF-α appears to have direct effects on endothelial cells which play a major role in inflammation and tissue injury. TNF-α induced the release of IL-1 from endothelial cells (Nawroth, P. O. et al. "J. Exp. Med." 163:1363 [1986]) and induces neutrophil adherence to endothelial cells (Gamble, J. R. et al. supra and Pohlman, T. H. et al., "J. Immunol." 136:4548 [1986]) via the CDW18 neutrophil membrane protein complex (also called the C3bi receptor/adherence glycoprotein mentioned earlier). Further evidence that the endothelium is a major site of TNF action in vivo comes from studies on effects of TNF-α on the hemostatic properties of endothelial cells (Nawroth, P. O. et al., "J. Exp. Med." 164:740 [1986]) in culture. Incubation with rTNF-α causes changes in the production of two activities: induction of tissue factor, a procoagulant cofactor protein (Bach, R. et al. "J. Biol. Chem." 256:8324 [1981] and Stern, D. M. et al., "Proc. Natl. Acad. Sci. USA" 82:2523 [1985]) and inhibition of formation of activated protein C, an anticoagulant cofactor protein (Esmon, N. et al., "J. Biol. Chem." 257:859 [1982]). Extensive changes in the morphology of human vascular endothelial cells in confluent primary culture treated with TNF-α have also been reported (Stolpen, A. H. et al., "Am. J. Pathol." 123:16 [1986]). TNF-α induces endothelial cell expression of Class 1 major histocompatibility antigens and procoagulant activity, as well as increasing endothelial cell adhesiveness for polymorphonuclear leukocytes (Nathan, C. F. "J. Clin. Invest." 79:319–326 [1987]; Buetler, B. et al. "Nature" 320:584–588 [1986]; and Le, J. et al., "Lab. Invest. " 56:234–248 [1987]). TNF-α has also been shown to inhibit growth and induce distinct morphological changes in cultured microvascular endothelial cells (Sato, N. et al. "Proc. Japan. Acad." 61:471–474 [1985]). TNF-α inhibits the chemokinetic response induced in BCE (bovine adrenal capillary endothelial cells) by tumor cell conditioned medium (Sato, N. et al., "J. Natl. Cancer Inst." 76:1113–1121 [1986]). None of these reports on the effects of TNF on endothelial cells teach or suggest that TNF is capable of inducing vascularization in vivo.

A number of intracellular TNF activities have been reported. They include stimulation of IL-1 and $PGE_2$ production in resting macrophages (Bashwich, P. R. et al., "Biochem. Biophys. Res. Commun." 136:94 [1986]), induction of class I (but not the immunologically more significant class II) protein antigens of the major histocompatibility complex (Collins, T. et al., "Proc. Natl. Acad. Sci. USA" 83:446 [1985]), induction of synthesis of collagenase and $PGE_2$ in synovial cells and dermal fibroblasts (Dayer, J. M. et al., "J. Exp. Med." 162:2163 [1985]), fragmentation of target-cell DNA into discretely sized pieces (Schmid, D. S. et al., "Proc, Natl. Acad. Sci. USA" 83:1881–1885 [1986]), induction of GM-CSF in normal human lung fibroblasts (Munker, G. J. et al., "Nature" 323:79 [1986]), stimulation of complement component C3 in human hepatoma cells (Darlington, G. J. et al., "J. Cell. Biol." 103:787 [1986]), and depression of cytochrome P450 and drug metabolizing enzymes (ethoxycoumarin deethylase and arylhydrocarbon hydroxylase) in mouse liver (Ghezzi, P. et al., "Biochem. Biophys. Res. Commun." 136:316 [1986]).

TNFs function in vivo in interrelated fashion with other monokines and lymphokines. In recent years it has become increasingly evident that cytokines acting locally, such as interleukins, interferons, etc., play an important and interdependent role in modifying biological responses. In the immune response, these mediators produce autocrine as well as paracrine effects during T and B cell activation (Friedman, R. M. et al., "Adv. Immunol." 34:97 [1983]). For instance, macrophages secrete IL-1, which induces T cells to secrete IL-2 and this in turn causes secretion of IFN-$\gamma$, which can cause the production of TNF-$\alpha$ and TNF-$\beta$. Human peripheral blood mononuclear cells (PBMC) were shown to be induced by rIL-2 to secrete both TNF-$\beta$ and TNF-$\alpha$, and the effect of IL-2 was augmented by rIFN-$\gamma$ (Svedersky, L. P. et al., "J. Immunol." 134:1604 [1985] and Nedwin, G. E. et al., "J. Immunol." 135:2492 [1985]). In some instances IFN-$\gamma$ by itself also induced TNF-$\alpha$/TNF-$\beta$ production (Wong, G. H. W. et al., *Sixth International Congress of Immunology*, Abstract No. 3.33.43, p. 365 [1986]). TNF-$\alpha$ production could be seen within 3 hours after induction, reaching peak levels at 48 hr and declining thereafter; TNF-$\beta$ production started at a slower rate, requiring greater than 8 hours and reached a peak in 72 hr; IFN-$\gamma$ did not alter the kinetics of TNF-$\alpha$/TNF-$\beta$ induction by IL-2 (Dinarello, C. A. et al., "J. Exp. Med." 163:1433 [1986]). Conversely, TNF itself was reported to have stimulated lymphocytes to secrete IFN-$\gamma$ (Wong, G. H. W. et al., supra), FS-4 fibroblasts to synthesize IFN-$\beta_2$ (Kohase, M. et al., supra), and endothelial cells (Nawroth, P. O. et al., supra), monocytes (Phillip, R. et al., "Nature" 323:86 [1986] and Dinarello, C. A. et al., supra), and macrophages (Bashwich, P. R. et al., supra) to release Il-1.

Besides regulation of TNF-$\alpha$/TNF-$\beta$ production by other cytokines, in order to fully comprehend the true physiological role of TNFs, one must also consider their relationship to the monokine IL-1 and the lymphokine, IFN-$\gamma$. There are many similarities between the biological action of TNFs and IL-1, and the presence of IFN-$\gamma$ together with TNFs results in markedly synergistic or antagonistic responses. These actions are briefly described below.

TNFs share a number of biological activities with IL-1, another distinct 17,000 Da protein produced by monocytes, which plays a major role in mediating the immune response (Matsushima, K. et al., "Cell. Immunol." 29:290 [1985]). Some common biological activities of these two monokines include: endogenous pyrogenic activity in vivo (Dinarello, C. A. et al., supra), induction of procoagulant activity in endothelial cells (Nawroth, P. O. et al., supra and Stern, D. M. et al., "J. Exp. Med." 162:1223 [1985]), stimulation of bone resorption and cartilage resorption, stimulation of collagenase and $PGE_2$ production in dermal fibroblasts (Dayer, J. M. et al., supra and Pujol, J. P., et al., "Exp. Cell. Res." 158:63 [1985]), suppression of lipoprotein lipase activity in adipocytes, stimulation of growth of fibroblasts (Matsushima, K. et al., supra), cytocidal activity against several neoplastic cell lines and anti-tumor activity in vivo. However, differences in biological activity between TNFs and IL-1 also exist, for example, TNF has a rapid direct cytostatic and cytotoxic activity against a wide variety of neoplastic tissues, whereas IL-1 requires coincubation for at least 48 hours for cytostasis, and this only with a single human melanoma cell line (A-375). IL-1 also has in vitro adjuvant activity for increasing specific cytotoxic T lymphocytes following coculture of "naive" lymphocytes with allogeneic stimulator cells, an in vitro property not shared with TNF. IL-1 does not activate PMN (Bevilacqua, M. P. et al., "J. Clin. Invest." 76:2003–2011 [November 1985]). IL-1 does not inhibit stem cell colony formation (Zucali, J. R. et al., "Blood" 69:33–37 [January 1987]).

Several investigators have found that the in vitro tumoricidal activity of TNFs is significantly augmented by coincubation with IFNs. IFN-$\alpha$, -$\beta$ or -$\gamma$, while not showing any antiproliferative effects by themselves, synergistically enhanced the cytotoxicity of TNF-$\alpha$/TNF-$\beta$. Synergism between IFN-$\gamma$ and TNF-$\beta$ has also been reported (Murphy, M. et al. "J. Exp. Med." 164:263 [1986]) for inhibition of hematopoietic cell differentiation. Furthermore, the synergistic effect of IFN-$\gamma$ appears to be correlated with its ability to induce synthesis of TNF receptors in target cells. It is unclear whether the synergism is solely explained by increased receptor number, or whether other proteins involved in the mechanism of cytotoxicity are also induced by IFN-$\gamma$.

In EP No. 168,214 it is suggested that TNF-$\alpha$ be formulated into sustained-release vehicles, particularly for implantation at surgical sites from which tumors have been removed. Copending U.S. Ser. No. 814,355, filed Dec. 27, 1985, teaches preparing topical foundations or water insoluble matrices (such as bandages) containing gamma interferon and TNF for use in treating nonmalignant hyperproliferative epidermal growths. Neither citation observes that TNF induces angiogenesis, nor is it specifically taught to administer TNF to the surface of a wound.

It is clear from the foregoing discussion that the in vivo mechanism of action of TNFs are complicated by virtue of their diverse biological effects, their interaction with other monokines and lymphokines, and the target tissues or cells involved.

The induction of vascularization is a critical component of the wound healing process. Vascularization ensures that proliferating and differentiating fibroblasts are supplied with nutrients and oxygen, and that elements of humoral and cellular immunity are delivered to sites of potential bacterial infection. It is desirable to induce neovascularization as early as possible in the course of wound healing, particularly in the case of patients having conditions that tend to retard wound healing, e.g. burns, decubitis ulcers, diabetes, obesity and malignancies. Even normal post-surgical patients will be benefited if they can be released from hospital care at any earlier date because of accelerated wound healing.

Another object of this invention is to determine the factor or factors secreted by macrophages which are responsible for macrophage neovascularization.

Another object of this invention is to provide novel compositions and methods for modulating angiogenesis.

These and other objects will be apparent from the description of the invention herein.

SUMMARY OF THE INVENTION

The objects of this Invention are accomplished by a method comprising treating a patient bearing a wound by applying an angiogenically active does of a TNF to the wound. The method of this invention facilitates the neovascularization of surgical incisions, burns, traumatized tissue, skin grafts, ulcers and other wounds or injuries where accelerated healing is desired.

Novel topical compositions containing a TNF are provided for use in the inventive method, as are novel articles such as sutures, grafts and dressings containing TNF.

DETAILED DESCRIPTION OF THE INVENTION

TNF includes TNF-$\alpha$ and TNF-$\beta$, together with amino acid sequence variants thereof which exhibit neovascularizing activity. Such variants include animal TNFs, alleles of animal or human TNF, and the products of site directed mutagenesis of the native TNF sequences.

The term "wound" is defined herein as any opening in the skin, mucosa or epithelial linings, most such openings generally being associated with exposed, raw or abraded tissue. There are no limitations as to the type of wound or other traumata that can be treated in accordance with this invention, such wounds including (but are not limited to): first, second and third degree burns (especially second and third degree); surgical incisions, including those of cosmetic surgery; wounds, including lacerations, incisions, and penetrations; and ulcers including decubital ulcers (bed-sores) and ulcers or wounds associated with diabetic, dental, haemophilic, malignant and obese patients. Although the primary concern is the healing of major wounds by neovascularization, it is contemplated that TNF may also be useful for minor wounds, and for cosmetic regeneration of epithelial cells. Preferably, the wounds to be treated are burns and surgical incisions, whether or not associated with viral infections or tumors. In most cases wounds are not the result of a tumor or a viral infection and ordinarily they do not include tumor cells.

TNF is preferably delivered to wounds by topical application, "topical" in this context meaning topical to the wound, and does not necessarily refer to epidermal application. When applied topically, the TNF is usually combined with other ingredients, such as carriers and/or adjuvants. There are no limitations on the nature of such other ingredients, except that they must be pharmaceutically acceptable, efficacious for their intended administration, and cannot degrade or inactivate TNF. TNF is applied to burns in the form of an irrigant or salve, and if so then in an isotonic solution such as physiological saline solution or D5W. TNF is particularly useful in accelerating the growth and survival of skin grafts applied to burns. Ordinarily, a TNF-containing composition is impregnated into the grafts or adherently coated onto the face of the graft, either on the side of the graft to be applied to the burn or on the exterior side of the graft. TNF also is included in burn debridement salves which contain proteases so long as the debridement enzyme does not proteolytically inactivate the TNF.

TNF is impregnated into surgical articles in accordance with this invention, such articles being defined as items to be contacted with wounds which articles are typically water adsorbent or hydratable and which have a therapeutic utility in treating wounds. Examples of surgical articles are dressings, sutures, pledgets, skin grafting films (including living skin grafts as well as collagen-containing membranes) and the like as will be known to the clinician. Dressings for use herein generally comprise water adsorbent laminates containing TNF to be adherently placed into contact with wounds. Improved dressings for use with TNF as described herein preferably will have a membrane such as a dialysis membrane interposed between the wound surface and the adsorbent substance in the dressing, the membrane containing pores sufficiently small for TNF to diffuse into the wound but not sufficiently large for epithelial cells to penetrate into the adsorbent. The degree of adsorbency will vary considerably and in fact dressings are included herein which are nonadsorbent, i.e., the TNF is deposited or stored in an aqueous reservoir which is used to irrigate the wound on a continuous or intermittent basis.

TNF also is formulated into ointments or suspensions, preferably in combination with purified collagen, in order to produce semisolid or suspension vehicles. Conventional oleoginous formulations containing TNF are useful as salves. Such TNF carriers and formulations release TNF on a sustained basis at the wound, thereby serving to create a chemotactic gradient that directionally orients neovascularization, e.g. into a skin graft. Sustained release formulations for TNF include semipermeable polymer matrices in the form of shaped articles, e.g. films, or microcapsules. Implantable sustained release matrices include copolymers of L-glutamic acid and gamma ethyl-L-glutamate (U. Sidman et al., "Biopolymers" 22(1):547-556 [1983]), poly (2-hydroxyethylmethacrylate) (R. Langer et al., "J. Biomed. Mater. Res." 15:167-277 [1981] and R. Langer "Chem. Tech.: 12:98-105 [1982]), ethylene vinyl acetate (R. Langer et al., Id.), or poly-D-(—)-3-Hydroxybutyric acid (EP No. 133,988A). These formulations may function as bioerodible matrices or as stable sources for the passive diffusion of TNF.

Sustained release TNF compositions for contact with wounds also include liposomally entrapped TNF. Liposomes containing TNF are prepared by methods known per se: DE No. 3,218,121A; Epstein et al., "Proc. Natl. Acad. Sci. USA" 82:3688-3692 [1985]; Hwang et al., "Proc. Natl. Acad. Sci. USA" 77:4030-4034 [1980]; EP Nos. 52322A; 36676A; 88046A; 143949A; 142641A; Japanese patent application No. 83-118008; U.S. Pat. Nos. 4,485,045 and 4,544,545; and EP No. 102,324A. Ordinarily the liposomes are of the small (about 200–800 Angstroms) unilamelar type in which the lipid content is greater than about 30 mol. % cholesterol, the selected proportion being adjusted for the optimal rate of TNF leakage.

TNF is formulated with other ingredients such as carriers and/or adjuvants, e.g. albumin, nonionic surfactants and other emulsifiers. There are no limitations on the nature of such other ingredients, except that they must be pharmaceutically acceptable, efficacious for their intended administration, and cannot degrade the activity of the active ingredients of the compositions.

TNF optionally is supplied with other known angiogenic agents such as TGF-α, TGF-β, fibroblast growth factor, epidermal growth factor and angiogenin, and the angiogenic activity of the combinations observed for synergistic effects. TNF optionally also is combined with an with an IFN, e.g. IFN-γ, and other cytokines, or may be free of interferons such as IFN-γ. Where such cytokines or known angiogenic agents are species-specific, the appropriate cytokine or agent will be selected for the species to be treated.

Animals or humans are treated in accordance with this invention. It is possible but not preferred to treat an animal of one species with TNF of another species. The preferred TNF for use herein is mature recombinant human TNF-α having the native Val Arg amino terminus and delivered at a concentration of about 50 ng/ml.

The amount of TNF to be contacted with the wound depends upon a great number of variables that will be taken into account by the clinician, including the presence of other angiogenic agents in the TNF formulations, the nature of the wound to be treated, the condition of the patient, the TNF formulation selected, the neovascularizing activity of the molecular species of TNF chosen and the route of administration. Lesser amounts of TNF typically are administered when the TNF is formulated into a sustained release vehicle, e.g. dressing or ointment, and when the TNF is administered by direct topical contact rather than impregnated into a bandage or dressing. The typical topical formulation will be capable of delivering a concentration of mature (ValArg N-terminal) human TNF-α at the neovascularization target site (for example, a skin graft) in a range of about from 0.25 ng/cc to 350 ng/cc, although this therapeutic dose range is subject to considerable variation as noted above. Delivery of concentrations outside of this range may offer certain of the benefits of TNF neovascularization, but the clinician will be expected to monitor dosages in order to optimize performance of TNF in wound healing. It also should be noted that the weight amount will vary for other TNF variants and forms if their molecular weight and/or angiogenic potency differ from that of mature human TNF-α. Potency differences are easily determined by comparing the degree of neovascularization achieved with the candidate TNF and mature human TNF-α in any of the assays set forth in the Examples herein.

The invention will be more fully understood in the light of the following examples, which will not be construed as limiting the scope of the invention.

EXAMPLE 1

Chemotaxis of bovine capillary endothelial cells was performed in 25 μl modified blind well Boyden chambers (Neuroprobe, Bethesda, MD). Briefly, 8 μm pore diameter polycarbonate filters were soaked in 0.5M acetic acid for 24 hrs., washed in distilled water, incubated for a further 24 hrs. in a 100 μg/ml solution of calf skin gelatin (Sigma, Type III) and air dried. TNF-α was prepared at the required concentrations in RPMI1640-1% FCS, and placed in the lower wells of the chamber. The chamber was then incubated for 4 hrs. at 37° C. in an atmosphere of 95% air/5% $CO_2$. At the end of the incubation, filters were removed, fixed in methanol and stained using a modified Wright's stain (Diff-Quik, American Scientific Products, McGaw Park, Ill.). Filters were mounted on glass slides and the number of cells that had migrated from the upper to the lower surface of the filter determined by counting ten high power (400×) fields per well under the light microscope. Results are expressed as the mean±standard error of the mean (SEM) for triplicate determinations. bFGF (fibroblast growth factor) (10 ng/ml) was used as a positive chemotactic control.

Macrophage-conditioned medium (MCM) was prepared using thioglycollate-induced peritoneal macrophages. C57/B1 mice (7–10 weeks old, Jackson Labs, Bar-Harbor, Mass.) were injected intraperitoneally with 3 ml Bacto thioglycollate broth (Difco, Detroit, Mich.). 5 days later, animals were sacrificed by cervical dislocation, and peritoneal exudate cells harvested by peritoneal lavage. $3 \times 10^6$ cells were plated in 10 cm plastic culture dishes in 3 ml DMEM-10% FCS and incubated for 1 hr. at 37° C. in a humidified chamber gassed with 5% $CO_2$/95% air. The cell layer was then washed ($\times 5$) with serum free medium, and incubated for 36 hrs. in DMEM-0.2% lactalbumin hydrolysate. Medium was harvested and concentrated ten fold using Centricon-10 (10,000 $M_r$ cut-off) microconcentrators (Amicon, Danvers, Mass.). For antibody treatment of TNF-α or MCM, aliquots (1–5 μl) of rabbit anti-murine TNF-α polyclonal antibody were added and incubated at 22° C. for 4 hrs. 10 ml of Immunobead matrix (BioRad, Richmond, Calif.), consisting of goat anti-rabbit immunoglobulin, heavy and light chain specific, bound to a spherical polyacrylamide bead support, was then added to each tube, and incubation continued, with gentle agitation for 2 hrs. The Immunobeads were removed by centrifugation, and the supernatants concentrated ($\times 10$), dialyzed against DMEM, and assayed for angiogenic, chemotactic and capillary tube forming activity. Control incubations were also performed using normal, non-immune rabbit serum. The results are shown in Table 1 below.

TABLE 1

| Chemotaxis of Bovine Adrenal Capillary Endothelial Cells (BCE's) | |
|---|---|
| Concentration of Test Substance | Number of BCE's per 10 high power fields (± S.E.M.) |
| TNF-α: | |
| 500 ng (14,000 U/ml) | 48 ± 5 |
| 50 ng (1,400 U/ml) | 79 ± 4.6 |
| 5.0 ng (140 U/ml) | 51 ± 3.5 |
| 0.5 ng (14 U/ml) | 31 ± 2 |
| Rabbit anti-TNF-α + 50 ng (1,400 U/ml) | 24 + 3 |
| Control medium (RPMI640-1% FCS) | 22 ± 4 |
| bFGF: 10 ng/ml | 72 ± 13 |
| Macrophage-conditioned medium (MCM) | 77 ± 7 |
| MCM + Rabbit anti-TNF-α | 25 ± 4.5 |

These results demonstrate that TNF-α potently induced chemotaxis of BCEs across gelatin-coated 8μ polycarbonate filters. Peak stimulation of chemotactic activity was observed at 5–50 ng/ml, but activity was seen at concentrations as low as about 0.5 ng/ml. The maximal migratory response (79.3±4.6 migrated cells/10 high power fields) was equivalent to or greater than that induced by 10 ng/ml bFGF.

EXAMPLE 2

This example demonstrates the neovascular response induced in corneas of rats 7 days following implantation of TNF-α impregnated Hydron (bovine collagen; Collagen Corp.) pellets.

Murine recombinant (r) TNF-α (Urban, J. L. et al., "Proc. Natl. Acad. Sci. USA" 83:5233–5237 [1986]) (approx. $2.9 \times 10^7$ U/mg) and polyclonal rabbit antibody to murine rTNF-α (1325 neutralizing units/μl) were produced at Genentech (South San Francisco, Calif.). The activity of TNF-α is based on its cytotoxicity toward murine L-M fibroblasts in the presence of actinomycin-D. One unit of TNF-α is defined as the reciprocal of the test dilution resulting in 50% cytotoxicity. Test samples were prepared at the appropriate dilution, and mixed with equal volumes of Hydron prepared as a 12% (w/v) solution in 95% ethanol. 10 μl droplets of this mixture were placed on the square cut ends of 2 mm diameter teflon rods (Berghoff, Raymond, N.H.) and allowed to dry under reduced pressure. These pellets were implanted in the corneas of F344 rats, approximately 1.5 mm from the corneal limbus, as described previously (Polverini, P. J. et al.. "Nature" 269:804–806 [1977] and Polverini, P. J. et al., "Lab. Invest" 51:635–642 [1985]). Corneas were monitored daily for ingrowth of new microvessels from the limbal vasculature toward the implants. Seven days after implantation, animals were perfused intraarterially with colloidal carbon (Pellikan, Hanover, FRG), and corneas were fixed and excised, to obtain a permanent record of the vascular pattern of growth.

Strong and sustained growth of new capillary blood vessels was found to have extended from the corneal limbus towards the Hydron implant containing 3.5 ng (0.2 pmoles) of TNF-α. Below 350 ng, corneas showed no clouding or edema, indicating that inflammation was not a significant component of the angiogenic reaction. This was confirmed by histological examination, which also indicated an absence of infiltrating leukocytes. Pellets containing more than 355 ng of TNF-α induced mild, transient edema, but no hemorraghic exudate was observed.

EXAMPLE 3

This example demonstrates TNF-α-induced neovascular responses in chick chorioallantoic membranes (CAM) or shelless egg cultures.

Fertilized chick eggs were cracked on the third day of gestation into plastic wrap cradles as described previously (Montesano, R. et al., "Cell" 42:469–477 [1985]). The shell-free embryos were incubated for 7 days at 37° C. in a humidified incubator, allowing normal development to proceed. Test samples were prepared by combining 1 volume of test substance at the required concentration with 9 volumes 0.5% (w/v) methyl cellulose in water. 10 μl droplets of the mixture were applied to the square cut ends of 2 mm Teflon rods, and allowed to dry. These pellets were then carefully placed on the developing chorioallantoic membrane of the shelless egg cultures. Growth of new blood vessels was monitored daily for 3 days following pellet application using a Wild M5A stereomicroscope (Heerbrug, Switzerland).

A strong neovascular response was induced by TNF-α on the developing chick CAM. TNF-α (3.5 ng per pellet) induced a great increase in the density of the microvascular bed in the region of the pellets, with apparent regression of larger vessels, while 35 ng of TNF-α induced a characteristic spokewheel pattern of new vessel growth. At higher concentrations, inflammatory responses were evident.

EXAMPLE 4

This example shows that capillary tube-like structures are formed from BCEs cultured on collagen gels.

The ability of test substances to induce BCE monolayers to organize into capillary tube-like structures that invade collagen gels was assayed by a modification of the procedures of Montesano and Orchi ("Cell" 42:469–477 [1985]). Collagen gels were prepared in 12-well culture plates (Costar, Vineland, N.J.) by combining 8 volumes bovine dermal collagen solution (Vitrogen, Collagen Corporation, Palo Alto, Calif.) (3.6 mg/ml in 0.012M HCl) with 1 volume 10× RPMI1640 and 1 volume 7.5% $NaHCO_3$ diluted 1:10 with 0.142M NaOH. One half ml buffered collagen solution was pipetted into the wells and allowed to gel overnight at 37° C. in an atmosphere of 95% $O_2/5CO_2$. BCEs were isolated and cloned from bovine adrenal cortex by the method of Folkman et al. ("Proc. Natl. Acad. Sci. USA") 76:5217–5221 [1979]) and cultured in DMEM-20% FCS. One ml BCEs ($2 \times 10^6$/ml) at passage 11 or 12 was seeded into each well. Plates were incubated until cultures reached confluence (2–3 days), washed, and TNF-α or control media at the appropriate concentrations were added. 24 hrs. later the cultures were washed with PBS, fixed with 2.5% paraformaldehyde-1% glutaraldehyde in cacodylate buffer, and then examined and photographed using a phase contrast microscope. Selected cultures were embedded in glycol methacrylate, sectioned, and processed for light microscopy. Bovine basic Fibroblast Growth Factor (bFGF) was purchased from R & D Systems (Minneapolis, MN) and used as a positive control.

Confluent cultures of BCE's exhibited distinct changes in morphology when cultured on collagen gels in the presence of TNF-α. 50 ng to as low as 3.5 ng/ml induced the formation of branching capillary tube-like structures that grew from the endothelial monolayer into the collagen gels within 24–48 hrs. At higher concentrations of TNF-α (>350 ng/ml) some rounding of cells followed by shedding from the gels was observed after 24–48 hrs. of incubation. This was not observed at lower concentrations.

EXAMPLE 5

In order to determine if the angiogenic activity produced by activated macrophages in culture was related to TNF-α, a polyclonal antibody to murine TNF-α was used in an attempt to neutralize biological activity. This antibody completely neutralized the angiogenic activity in conditioned medium of thioglycollate-induced peritoneal macrophages, indicating that the macrophage-derived angiogenic agent is either identical or immunologically closely related to TNF-α. This neutralization of activity was demonstrated using the rat cornea, the chick CAM, and the BCE chemotactic and capillary tube formation assays.

Our data strongly suggest that TNF-α is a potent mediator of angiogenesis, and with activity at concentrations as low as 3.5 ng (approx. 0.2 picomoles) per implant in both the rat cornea and the chick CAM. This compares with published reports for induction of corneal neovascularization for acidic and basic FGF of 0.33–0.5 pmoles (6–10 ng) (Shing, Y. et al., supra; Thomas, K. A. et al., supra; and Esch, F. et al., supra), for angiogenin of 3.5 pmoles (50 ng) (Fett, J. W. et al., supra), and of angiogenic induction in the hamster cheek pouch by 10 μg (2 nmoles) Epidermal Growth Factor (EGF) and 0.3–1 μg Transforming Growth Factor-α (TGF-α) (Schreiber, A. B. et al., supra). TNF-α thus appears to be angiogenic at concentrations comparable to, or lower than those reported for FGF, angiogenin, EGF and TGF-α.

We claim:

1. A method for accelerating the neovascularization of a wound which comprises applying to the wound an angiogenically effective dose of a composition comprising tumor necrosis factor.

2. The method of claim 1 wherein the composition is applied topically by direct contact with the wound and the wound is a fresh surgical incision.

3. The method of claim 2 wherein the composition further comprises a sustained release carrier.

4. The method of claim 3 wherein the composition further comprises a bioerodible polymer.

5. The method of claim 4 wherein the bioerodible polymer is a polylactide.

6. The method of claim 2 wherein the composition further comprises collagen.

7. The method of claim 2 wherein the TNF is human TNF-α.

8. The method of claim 2 wherein the wound is a burn and the composition further comprises a skin graft.

9. The method of claim 2 further comprising administering to the wound a substance selected from the group of growth factors, antibiotics, debridement agents and angiogenin.

10. The method of claim 9 wherein the growth factor is TGF-α, TGF-β, fibroblast growth factor, or epidermal growth factor.

11. The method of claim 9 wherein the antibiotic is a silver salt.

12. The method of claim 2 wherein the wound is a diabetic or decubitus ulcer.

13. The method of claim 3 wherein the sustained release carrier is an oleaginous salve.

14. The method of claim 3 wherein the carrier is in the form of a film.

15. The method of claim 1 wherein the TNF is applied to the wound by substantially continuous irrigation.

* * * * *